United States Patent [19]
Bockrath et al.

[11] Patent Number: 6,008,384
[45] Date of Patent: Dec. 28, 1999

[54] METHOD AND RU,RE,SN/CARBON CATALYST FOR HYDROGENATION IN AQUEOUS SOLUTION

[75] Inventors: Richard Edmond Bockrath; Daniel Campos, both of Wilmington, Del.; Jo-Ann Theresa Schwartz, Chadds Ford, Pa.; Richard Thomas Stimek, Laplace, La.

[73] Assignee: E. I. du Pont de Nemours and Company, Wilmington, Del.

[21] Appl. No.: 09/033,992

[22] Filed: Mar. 3, 1998

[51] Int. Cl.$^6$ .................. C07D 307/08; C07D 307/58; C07C 27/04; C07C 29/149
[52] U.S. Cl. .................. 549/508; 549/325; 549/326; 502/185; 568/864
[58] Field of Search .................. 549/325, 326, 549/508; 568/864; 502/185

[56] References Cited

U.S. PATENT DOCUMENTS

| | | | |
|---|---|---|---|
| 3,138,560 | 6/1964 | Keith et al. | 252/447 |
| 4,550,185 | 10/1985 | Mabry et al. | 549/508 |
| 4,609,636 | 9/1986 | Mabry et al. | 502/183 |
| 4,659,686 | 4/1987 | Griffiths et al. | 502/183 |
| 4,985,572 | 1/1991 | Kitson et al. | 549/326 |
| 5,073,650 | 12/1991 | Stabel et al. | 568/864 |
| 5,149,680 | 9/1992 | Kitson et al. | 502/185 |
| 5,196,602 | 3/1993 | Budge et al. | 568/864 |
| 5,478,952 | 12/1995 | Schwartz | 549/325 |

FOREIGN PATENT DOCUMENTS

| | | | |
|---|---|---|---|
| 5-246915 | 9/1993 | Japan | C07C 29/149 |
| 6-116182 | 4/1994 | Japan | C07C 29/149 |
| 6-157490 | 6/1994 | Japan | C07D 307/08 |
| 6-157491 | 6/1994 | Japan | C07D 307/08 |
| 6-179667 | 6/1994 | Japan | C07D 307/08 |
| 7-165644 | 6/1995 | Japan | C07C 31/20 |
| 9-59190 | 3/1997 | Japan | C07C 31/20 |

OTHER PUBLICATIONS

Junichi Kanetaka et al., Hydrogenation Of Maleic Anhydride And Intermediates By Nickel–Rhenium Catalyst Supported On Kieselguhr, *Bulletin Of The Japan Petroleum Institute*, 12, 89–96, May 1970.

S. B. Ziemecki et al., Surface Mobility of $Re_2O_7$ in the System $Re^7+Pd^0/\gamma-Al_2O_3$, *Academic Press, Inc.*, 207–217, Jan. 3, 1986.

*Primary Examiner*—Bernard Dentz

[57] ABSTRACT

An improved two step (dual stage catalysis) aqueous hydrogenation process and a novel trimetallic hydrogenation catalysts consisting essentially of highly dispersed, reduced ruthenium and rhenium metals in the presence of a third metal tin on carbon support particular useful in the second stage of the process. Such process and catalyst exhibit high conversion rates in aqueous solution hydrogenation of hydrogenatable precursors (e.g., maleic acid, succinic acid, corresponding esters, γ-butyrolactone, etc.) to tetrahydrofuran, γ-butyrolactone, 1,4-butanediol and mixtures thereof wherein the relative molar ratio of 1,4-butanediol to tetrahydrofuran products being produced can be controlled.

11 Claims, 2 Drawing Sheets

METHOD AND RU,RE,SN/CARBON CATALYST FOR HYDROGENATION IN AQUEOUS SOLUTION

BACKGROUND OF THE INVENTION

1. Field of the Invention

This invention relates to an improved two step or dual stage aqueous hydrogenation process and a novel trimetallic ruthenium, rhenium, tin on carbon support (Ru,Re,Sn/carbon) catalyst particularly useful in the process. More specifically but not by way of limitation, the invention relates to the production of tetrahydrofuran, γ-butyrolactone, 1,4 butanediol and the like from a hydrogenatable precursor such as maleic acid, succinic acid, corresponding esters and their mixtures or the like in aqueous solution in the presence of hydrogen and a catalyst consisting essentially of highly dispersed, reduced ruthenium and rhenium in the presence of tin on a carbon support.

2. Description of the Related Art

Various methods and reaction systems have been proposed in the past for manufacturing tetrahydrofuran, γ-butyrolactone and 1,4-butanediol by catalytic hydrogenation of maleic acid, maleic anhydride, succinic acid and/or related hydrogenatable precursors. Also, a variety of hydrogenation catalyst have been historically proposed for this purpose including various transition metals and combinations of transition metals deposited on various inert supports, all as generally known in the art. For example, U.S. Pat. Nos. 4,985,572 and 5,149,680 disclose and claim a process for hydrogenating a carboxylic acid or an anhydride thereof to corresponding alcohol and/or carboxylic acid ester using a catalyst composition comprising an alloy of a noble metal of Group VIII and one other metal. In a comparative test a ruthenium and rhenium supported on graphitized carbon is used as a catalyst in a plug flow single pass hydrogenation of acetic acid. Also, Japanese patent application publications (Kokai) 6-157490, 6-179667 and 6-157491 disclose methods of preparing tetrahydrofuran by catalytic hydrogenation of maleic anhydride or maleic acid under milder conditions in the presence of an acidic substance using as catalyst a rhenium compound and a Group VIII metal in the first two references and a ruthenium compound in the latter. Comparative examples in the first two references illustrated the use of a ruthenium and rhenium on carbon catalyst without the acidic substance being present. However as a general rule these proposed catalytic reactions are predominantly conducted in an organic solvent or organic reaction media and not in an aqueous solution phase. In fact, at least one prior publication suggests that water and succinic acid may be considered as inhibitors to the desired catalysis, see Bulletin of Japan Petroleum Institute, Volume 12, pages 89 to 96 (1970). One notable exception to the lack of aqueous phase catalytic hydrogenation is the use of a carbon supported catalyst comprising 0.5% to 10% palladium and about 1% to 10% rhenium by total weight of supported catalyst in an aqueous solution hydrogenation reaction wherein the palladium is present on the carbon support in the form of crystallites having an average size of about 10 nm to 25 nm and the rhenium is present in a highly dispersed phase having an average size less than about 2.5 nm as described in U.S. Pat. Nos. 4,550,185; 4,609,636; and 4,659,686. Also, in a recently laid-open Japanese Kokai 5-246915, Sep. 24, 1993, the use of reduced ruthenium and tin on an activated carbon support is disclosed in aqueous phase catalytic hydrogenation. This reference teaches the use of any Group VIII noble metal including palladium and ruthenium in combination with either tin, rhenium or germanium. The reference distinguishes the claimed subject matter from the previous Pd, Re/Carbon aqueous phase hydrogenation system of the prior art by virtue of specifically claiming the use of a carrier of porous carbon having a BET surface area of at least 2,000 $m^2/g$; a concept and limitation that is not characteristic of the Pd, Re/Carbon system of the U.S. Pat. Nos. 4,550,185 and 4,609,636 nor is this limitation of any critical significance relative to the present invention.

In U.S. Pat. No. 5,478,952 a highly effective catalyst for aqueous phase hydrogenation is disclosed. This catalyst consists of Ru,Re/C wherein both metal components are present in a highly dispersed reduced state on a carbon support which is characterized by a BET surface area of less than 2,000 $m^2/g$. Said catalyst is characterized by a space-time-yield (STY) for conversion of maleic acid to tetrahydrofliran in excess of 600 grams of product per kilogram of catalyst per hour at 250° C. and 2,000 psig ($14\times10^6$ Pa) pressure.

Japanese patent application publication (Kokai) 7-165644 describes the use of a catalyst, obtained by supporting tin, ruthenium and at least one element selected from platinum and rhodium on a support, for the manufacture of 1,4-butanediol and/or tetrahydrofuran by a contact hydrogenation reaction which can be conducted in a variety of solvents including water, using as starting materials maleic anhydride, maleic acid, succinic anhydride, succinic acid, γ-butyrolactone or mixtures thereof. Various supports, including activated charcoal can be used and the metal components can be supported each in an amount of 0.5 to 50 wt % of the total catalyst. Tin in an amount 0.1 to 5 times by weight with respect to the transition metal components is usually preferred for the sake of enhancing product selectivity.

Japanese patent application publication (Kokai) 6-116182 describes catalysts comprising a combination of Group VIII noble metals with one or more metals selected from tin, rhenium, and germanium on a titania and/or alumina-modified silica support for the hydrogenation of organic carboxylic acids and/or organic carboxylic esters. The hydrogenation can be conducted in a variety of solvents including water. There is no special limitation on the type of organic carboxylic acid (including carboxylic anhydride) and/or organic carboxylic esters used in the hydrogenation reaction. For example, by using maleic anhydride and/or succinic anhydride in the hydrogenation reaction, 1,4-butanediol, γ-butyrolactone and tetrahydrofuran are produced.

BRIEF SUMMARY OF THE INVENTION

The present invention provides a novel trimetallic ruthenium, rhenium, tin catalyst supported on carbon that exhibits certain advantages when employed during hydrogenation of a hydrogenatable precursor in an aqueous solution. As such, this trimetallic catalyst of the instant invention and the process of using this catalyst may be viewed as an improvement of the bimetallic ruthenium, rhenium supported on carbon (Ru,Re/C) catalyst of U.S. Pat. No. 5,478,952. More specifically, it has now been discovered that the incorporation of tin into the previously known ruthenium and rhenium catalyst leads to better (improved) control of selectivity of production amongst the more useful products, such as tetrahydrofuran, 1,4 butanediol, and γ-butyrolactone concurrently with reduced relative production of undesirable by-products, such as n-butanol, n-propanol and volatile hydrocarbons such as methane, ethane, propane and butane. Although not confirming possible explanation for the above discovery to any single rationale or theory, it is currently felt that the presence of relatively small amounts of tin in combination with the ruthenium and rhenium actually slows down the overall rate of hydrogenation and improves selectivity to desired products. In particular, these discoveries have led to the use of the novel trimetallic catalyst in a two-stage operation wherein the relatively fast hydrogenation of the double bond of maleic acid to produce succinic acid is achieved in a first stage using a prior art catalyst system followed by energy removal and/or temperature control and a subsequent second stage hydrogenation of the succinic acid to 1,4-butanediol, γ-butyrolactone and tetrahydrofuran using the Ru,Re,Sn/C catalyst of the instant invention. In this two-stage process the selection and/or control of the temperature in the second hydrogenation reaction will tend to determine the selectivity of desired products being produced; more specifically the molar ratio of 1,4-butanediol to tetrahydrofuran. It has been further discovered that this two-stage hydrogenation process can be advantageously employed when using the bimetallic Ru,Re/C catalyst of U.S. Pat. No. 5,478,952 in the second stage provided the temperature in this second hydrogenation step is reduced significantly; e.g., less than 175° C. and preferably 130 to 135° C.

Thus the present invention provides an improved hydrogenation catalyst consisting essentially of from 0.5 to 10% by weight ruthenium, from 2.0 to 20% by weight rhenium supported on carbon, the percentages based on total weight of supported catalyst, wherein both ruthenium and rhenium are present in a highly dispersed reduced state and from 0.1 to 5.0% by weight tin supported on the carbon wherein the carbon support is characterized by a BET surface area of less than 2,000 $m^2/g$. In addition, present invention provides for the general use of this trimetallic composition for catalytic hydrogenation of a hydrogenatable precursor in an aqueous solution comprising the steps of:

(a) hydrogenating a hydrogenatable precursor in an aqueous solution in the presence of hydrogen and a catalyst, said catalyst consisting essentially of from 0.5 to 10.0% by weight ruthenium, from 2.0 to 20.0% by weight rhenium supported on carbon, said percentages based on total weight of supported catalyst, wherein both ruthenium and rhenium are present in a highly dispersed reduced state and from 0.1 to 5.0% by weight tin supported on said carbon wherein said carbon support is characterized by a BET surface area of less than 2,000 $m^2/g$; and then (b) recovering at least one hydrogenated product.

Typically in the above process the hydrogenatable precursor is selected from the group consisting of maleic acid, maleic anhydride, flumaric acid, succinic acid, maleic acid, the esters corresponding to these acids, γ-butyrolactone and mixtures thereof.

More specifically, the present invention provides a two-stage method for catalytic hydrogenation of maleic acid in an aqueous solution comprising the steps of:

(a) hydrogenating maleic acid in an aqueous solution in the presence of hydrogen and a first catalyst to produce an aqueous succinic acid solution;

(b) hydrogenating said succinic acid solution produced in step (a) in the presence of hydrogen and a second catalyst, said second catalyst consisting essentially of (i) from 0.5 to 10% by weight ruthenium, (ii) from 2.0 to 20% by weight rhenium supported on carbon, said percentages based on total weight of supported catalyst, wherein both ruthenium and rhenium are present in a highly dispersed reduced state and (iii) up to 5.0% by weight tin supported on said carbon wherein said carbon support is characterized by a BET surface area of less than 2,000 $m^2/g$, such as to produce a mixture of 1,4-butanediol, γ-butyrolactone, and tetrahydrofuran wherein the selection of said second catalyst and said temperature for the hydrogenation of the succinic acid solution establishes the ratio of 1,4-butanediol to tetrahydrofuran being produced; and then (b) recovering at least one product selected from the group consisting of 1,4-butanediol, γ-butyrolactone and tetrahydrofuran.

Typically in this process the preferred temperature for the hydrogenation of the succinic acid solution is from 130 to 250° C. Preferably the temperature of the second stage (reactor inlet temperature) is selected from about 150 to about 210° C. when the trimetallic catalyst is employed (i.e., tin is present) and typically the molar ratio of 1,4-butanediol to tetrahydrofuran produced is from 5:1 to 1:1 across this respective temperature range. Preferably the temperature of the second stage (again measured as gas inlet/feed temperature) is controlled below 175° C. and most preferably at about 135° C. when the bimetallic catalyst is used. In one embodiment the process further comprises the step of removing heat energy from the succinic acid solution during hydrogenation.

It is an object of the present invention to provide an improved trimetallic catalyst system and methods of using the same involving ruthenium, rhenium and tin supported on carbon wherein the presence of the third metal tin results in the conversion of hydrogenatable precursor in aqueous solution at high conversion rates consistent with large scale commercial operations with significantly lower over-hydrogenation and production of undesirable by-products. It is a further object of the present invention to provide such a novel two-stage hydrogenation process that exhibits advantages when used with the previously known bimetallic catalyst and when employed with the instant trimetallic catalyst system affords the opportunity to selectively control the relative distribution of desirable products when producing 1,4-butanediol and tetrahydrofuran. Fulfillment of these objects and the presence and fulfillment of additional objects will be apparent upon complete reading of this specification and attached claims.

DETAILED DESCRIPTION OF THE INVENTION

Figure 1:
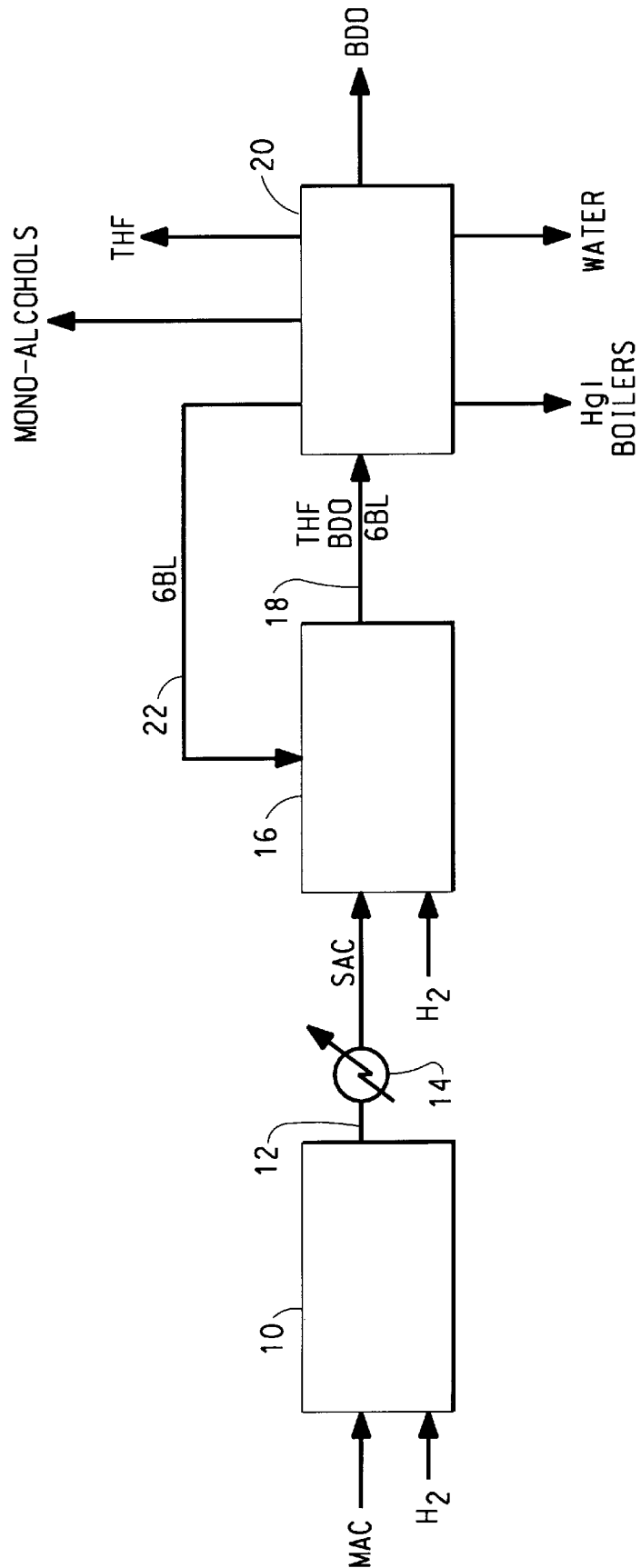
FIG. 1 is a schematic block diagram illustrating one specific embodiment of the two-stage hydrogenation process according to the present invention.

The hydrogenation catalyst according to the present invention involves both ruthenium and rhenium being present on a porous carbon support in a reduced, highly dispersed state in a manner analogous to the Ru,Re/C catalyst disclosed in U.S. Pat. No. 5,478,952 herein incorporated by reference. In addition, the catalyst of the present invention contains an effective amount of the third metal tin supported on the carbon. As suggested herein, the presence of the tin is presently viewed as moderating the high catalytic activity of the previous Ru,Re/C bimetallic catalyst system such as to afford improved control of selectivity during hydrogenation at commercial scale operation. The use of the two-stage process of the present invention in combination with selection of catalyst and reaction conditions results in superior yield of desired products and control of the molar ratio of 1,4-butanediol to tetrahydrofuran being produced without significantly promoting over-hydrogenation and production of undesirable by-products. Consistent with this view, the respective lower limit or minimum loading of ruthenium and rhenium metals on the carbon support is somewhat higher than the bimetallic system of the prior art in order to at least partially compensate for the presence of tin. Thus the trimetallic catalyst comprises at least 0.5% by weight of ruthenium metal and at least 2.0% by weight rhenium metal based on total weight of catalyst to insure at least reasonable catalyst activity when tin is present at 0.1 to about 5.0% by weight. The upper limit of the ruthenium and rhenium metal loading on the carbon support will be about 10% by weight ruthenium and about 20% by weight rhenium; preferably, 3.0% Ru and 9.0% Re. However, it should be appreciated that concentrations of ruthenium and rhenium above these upper limits may be operative and as such should be considered equivalent for purposes of the present invention but are felt to offer little advantage in terms of convenience and/or cost. Also, in view of the known mobility of rhenium (see S. B. Ziemecki. G. A. Jones and J. B. Michel, "Surface Mobility of $Re_2O_7$ in the System $Re^{7+}Pd^0/\gamma$-$Al_2O_3$", Journal of Catalysis 99, pp. 207–216, 1986), thus suggesting at least the possibility of migration of the rhenium over sustained use and aging of the catalyst, preferably the rhenium content initially is near the upper limit of the range. A preferred catalyst for hydrogenation of maleic acid to 1,4-butanediol and tetrahydrofuran contains about 1.0% ruthenium, about 6.0% rhenium and about 0.9% tin.

The carbon support useful in the present invention can be generally any such material as commonly known and commercially available for use in this art. Preferably the carbon catalyst support is a porous particulate solid characterized by a size distribution typically ranging from 5 to 100 microns for slurry applications and from about 0.8 to 4 mm for fixed bed applications and a BET surface area typically ranging from a few 100 to nearly 2,000 $m^2$/g. Preferably the carbon support will be commercially available material having an average particle size of the order of 20 microns for slurry applications and 3 mm for fixed bed applications and a BET surface area from about 700 to about 1,600 $m^2$/g. The catalyst support can be manufactured such as to have a latent acid, neutral or basic pH. Optionally, the catalyst support can be treated prior to metal deposition by one or more techniques as generally known in the art such as impregnation with alkali metal salts and/or calcination or acid wash.

The actual method of preparing the highly dispersed, reduced ruthenium and rhenium in the presence of tin on carbon catalyst according to the present invention can be generally any such process as known in the art that produces the desired high dispersion of ruthenium and rhenium provided tin is also incorporated onto the carbon. As such, the three distinct methods of catalyst preparation described in U.S. Pat. No. 5,478,952 are useful for purposes of this invention. In particular, a preferred method is to prepare a water solution or individual water solutions of a soluble ruthenium compound, a soluble rhenium compound and a soluble tin compound and then add this solution or these solutions to the carbon support. The water is then evaporated thus depositing the ruthenium, the rhenium and the tin compounds on the carbon support. The actual method of adding the solution to the support can be by any technique generally known to the art including by way of example but not by way of limitation; immersion, spraying, incipient wetness or the like. The dry or partially dried composite material is then subjected to a reducing atmosphere for a fixed period of time. Optionally the catalyst precursor may be added directly to the hydrogenation reactor wherein the reduction of the metal compounds on the carbon occurs in situ in the hydrogenation reactor.

It should be further appreciated that various other methods or alternate modes of depositing the ruthenium, rhenium and tin compounds on the carbon support, such as by selective precipitation or the like optionally with or without solvent washing to selectively remove less desirable companion anions all as generally known in the art, are contemplated as being equivalent methodologies for use in preparing the catalyst according to the present invention. This would also include the simultaneous or sequential deposition of the individual metal components.

The ruthenium compounds useful in the present invention for preparing the catalyst can be generally any such compound that is either water soluble or can be readily converted to a water soluble or partially water soluble compound that can then be deposited on the carbon support. This would include by way of example but not by way of limitation such compounds as $RuCl_3.xH_2O$, $Ru(NO)(NO_3)_3$ and the like. Preferably ruthenium trichloride is used.

The rhenium compounds useful in the present invention for preparing the catalyst can be generally any such compound that is either water soluble or readily converted to a water soluble or partially water soluble rhenium compound by the action of an oxidizing acid solution, hydrogen peroxide, or the like. As such, the perrhenate aqueous chemistry including the corresponding rhenium oxide deposition is particularly useful. Preferably a perrhenic acid solution is employed.

The tin compounds useful in the present invention for preparing the catalyst can be generally any such compound that is either water soluble or can be readily converted to a water soluble or partially water soluble compound that can then be deposited on the carbon support. This would include by way of example but not by way of limitation such compounds as $SnCl_2$, $SnCl_4$, $Na_2SnO_3$, $Sn(NO_3)_2$, $SnC_2O_4$ and the like. Typically $SnCl_4$ or $Na_2SnO_3$ are used because of availability and cost advantage.

The reducing agent employed to chemically reduce the ruthenium and/or rhenium can generally be any such reductant or reducing environment consistent with either liquid phase reduction or vapor phase reduction including by way of example but not by way of limitation; formaldehyde, hydrazine hydrate, hydroxylamine, sodium hypophosphite, sodium formate, glucose, acetaldehyde, sodium borohydride, hydrogen and the like. When a vapor phase reduction is employed involving gaseous hydrogen with or without an inert diluent gas such as nitrogen or the like in the presence of the solid catalyst precursor, typically the vapor phase reduction is performed at a temperature range of 100 to 500° C. (preferably 250 to 300° C.) at atmospheric pressure or up to a pressure of 3,000 psig ($2.07 \times 10^7$ Pa).

For purposes of the present invention a hydrogenatable precursor can be, in the broadest sense, any compound or material that can be chemically reduced by hydrogenation or hydrogen up-take. This would include, in particular but again not by limitation, various organic compounds containing unsaturation or oxygenated organic functional groups or both. Most particularly, the aqueous phase catalytic hydrogenation of maleic acid to γ-butyrolactone, 1,4-butanediol and tetrahydrofuran is illustrative of the utility of the method according to the present invention. In this regard and as illustrated in the examples, it should be appreciated that various products of the sequential hydrogenation reaction are also potential hydrogenatable precursors. In other words, in the conversion of maleic acid to tetrahydrofuran, the chemical reduction is known to be sequential involving the rapid addition of hydrogen across the double bond thus converting maleic to succinic acid followed by the slower addition of hydrogen forming potential intermediates such as γ-butyrolactone and/or 1,4-butanediol and ultimately tetrahydrofuran (corresponding to the up-take of five moles of $H_2$ and production of three mole of $H_2O$ per mole of THF). In commercial production the overall selectivity to THF production can be significantly influenced by optimizing reaction conditions including maintaining adequate acidity thus favoring ring closure and cyclic ether production at the expense of diol production, continuous vapor removal of the more volatile products, and subsequent separation and recycle of the lactone. However, heretofore the optimization of the selectivity to 1,4-butanediol during commercial production particularly when using a highly active hydrogenation catalyst has been limited. Clearly in these cases the γ-butyrolactone can be viewed as either a co-product or as a recycled hydrogenatable precursor reactant.

The method of using the highly dispersed, reduced ruthenium and rhenium in the presence of tin on carbon catalyst to hydrogenate a hydrogenatable precursor according to the present invention can be performed by various modes of operation as generally known in the art. Thus the overall hydrogenation process can be by use of a fixed bed reactor, various types of agitated slurry reactors, either gas or mechanically agitated or the like operated in either a batch or continuous mode, wherein an aqueous liquid phase containing the hydrogenatable precursor is in contact with a gaseous phase containing hydrogen at elevated pressure and the particulate solid catalyst. Typically such hydrogenation reactions are performed at temperatures from about 100° C. to about 300° C. in sealed reactors maintained at pressures from about 1,000 to about 3,000 psig ($7 \times 10^6$ to about $21 \times 10^6$ Pa).

When the trimetallic Ru,Re,Sn/C catalyst of the present invention is used to hydrogenate a hydrogenatable precursor such as to produce 1,4-butanediol and tetrahydrofuran at a desired or controlled molar ratio, the hydrogenation reaction is advantageously performed at a temperature below about 225° C. and above about 150° C. To obtain a high 1,4-butanediol to tetrahydrofuran BDO/THF) molar ratio the hydrogenation to these desired products should advantageously be performed at or near the lower end of this temperature range. Thus a BDO/THF molar ratio of as high as 5:1 has been achieved at the lower end of this temperature range while a BDO/THF molar ratio of 1:1 is more characteristic of the upper end of the temperature range (for fixed bed reactors). The method and conditions as well as the mode of operation will also influence advantageously the BDO/THF molar ratio during hydrogenation. For example, the liquid phase removal of products from the hydrogenation reactor will tend to enhance and maximize 1,4-butanediol production rather than tetrahydrofuran. In contrast, continuous vapor removal of product from the hydrogenation reactor will tend to maximize tetrahydrofuran production at the expense of 1,4-butanediol. Thus, as a practical consideration, low temperature liquid product removal intended to optimize 1,4 butanediol production favors the use of fixed bed catalytic reactor. On the other hand, high temperature vapor phase product removal intended to optimize tetrahydrofuran production favors the use of a slurry or stirred reactor.

One particularly advantageous method of using the trimetallic Ru,Re,Sn/C catalyst of the present invention to convert maleic acid in aqueous solution to 1,4-butanediol and tetrahydrofuran involves a two-stage hydrogenation process. In this two-stage hydrogenation process the hydrogenation of starting maleic acid to succinic acid is performed in a first hydrogenation reactor while the hydrogenation of the succinic acid to desired products is performed in a second and separate hydrogenation reactor. In this manner, the fast addition of hydrogen to the double bond of the maleic acid is isolated from the remaining conversion to desired products. Since the first hydrogenation is exothermic and isolated sequentially from the second hydrogenation, the heat of reaction can be advantageously removed or used to preheat the feed to the second reactor resulting in improved control of the temperature in the second hydrogenation reactor. In such a two-stage hydrogenation method either the bimetallic Ru,Re/C or the trimetallic Ru,Re,Sn/C catalyst is employed in the second hydrogenation reactor such as to take advantage of the control of the product distribution between 1,4-butanediol and tetrahydrofuran and thus higher yield to desired product and less over-hydrogenation to undesirable alkane product. Any of the commercially available hydrogenation catalysts as generally known in the art, e.g., 1% Pd on carbon or the like, can be employed in the first hydrogenation reactor.

One preferred embodiment of this two-stage process is illustrated conceptually in FIG. 1. As shown, an aqueous maleic acid solution (MAC) and hydrogen ($H_2$) are continuously introduced into the first stage hydrogenation reactor 10 wherein the maleic acid is catalytically reacted with the hydrogen to produce succinic acid. Preferably this first stage reactor is a fixed bed reactor involving typically a palladium on carbon catalyst system or the like. The effluent succinic acid solution (SAC) from the first stage reactor 10 is passed via line 12 through a heat exchanger 14 before entering the second stage hydrogenation reactor 16 containing the trimetallic Ru,Re,Sn/C catalyst of the present invention or the bimetallic Ru,Re/C catalyst. In this manner the heat of reaction associated with the addition of hydrogen to the double bond of the maleic acid can be substantially removed prior to the critical hydrogenation of succinic acid to desired product 1,4-butanediol (BDO), γ-butyrolactone (GBL), and tetrahydrofuran (THF). Additional hydrogen is also continuously added to this second reactor 16. The aqueous solution from the second hydrogenation reactor 16 is then passed via line 18 to a set of distillation columns 20 for separation and recovery of products. As illustrated in this particular embodiment, GBL recovery and recycle loop 22 is provide to optimize conversion to the commercially desirable BDO and THF. Typically and as shown, the more volatile THF as well as mono-alcohols and any trace hydrocarbons are separated and removed overhead.

It should be appreciated that in actual commercial practice of the specific embodiment being illustrated in FIG. 1, the individual hydrogenation reactors may alternatively be a plurality of reactors. Similarly the distillation columns can be any separation technique as generally known in the art. As such, these alternatives should still be considered within the scope of the present invention being disclosed and claimed are to be considered equivalents for purposes of this invention. Furthermore the presence of the GBL recycle loop should be considered optional particularly in situations wherein GBL is to be a co-product.

Figure 2:
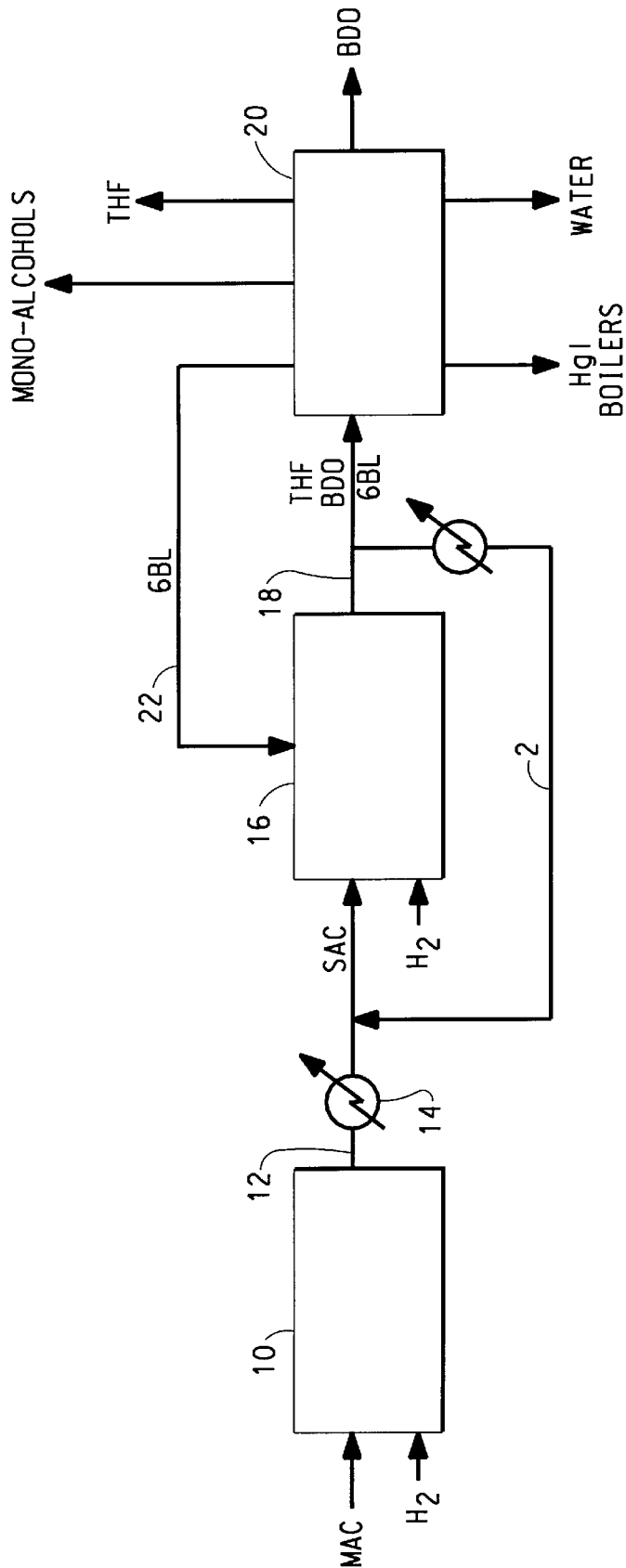
FIG. 2 is a schematic block diagram of another specific embodiment of the process illustrated in FIG. 1.

FIG. 2 illustrates an alternate embodiment of the two-stage process illustrated in FIG. 1 wherein again an aqueous MAC solution and $H_2$ are first converted to succinic acid in a first stage reactor 10 followed by the hydrogenation of the SAC solution in the second stage reactor 16. This particular specific embodiment includes a recycle loop 24 wherein a portion of the effluent from the second stage reactor 16 is direceted back through heat exchanger 24 to the inlet of the second stage reactor 16. In this manner the heat rise across the second hydrogenator is reduced and temperature control of the second stage is achieved. This embodiment is particularly useful when the second stage hydrogenation is a fixed bed reactor that is intended to be operated at low temperature in order to preferentially produce BDO at the expense of THF production.

The following examples are presented to more fully demonstrate and further illustrate various individual aspects and features of the present invention while the comparative examples and showings are intended to further illustrate the differences and advantages of the present invention. As such the examples are felt to be non-limiting and are meant to illustrate the invention but are not meant to be unduly limiting in any way.

EXAMPLE 1 THROUGH 9

To evaluate the carbon supported catalysts produced according to the present invention, a series of batch hydrogenation reactions were performed using γ-butyrolactone as the hydrogenatable precursor (i.e. reactant). The equipment employed was a 300 mL batch stirred autoclave made of Hastelloy C and supplied by Autoclave Engineers of Erie, Pa. The autoclave was equipped with a magnetically driven stirrer, with several top ports which were connected to a pressure cell, cooling coil, a thermowell, and a sample dip tube with a 7-micron fritted filter for removing reactor samples under process pressure and temperature. The hydrogen and nitrogen used were CP grade from a cylinder, the γ-butyrolactone, 99% pure, was supplied by B.F. Aldrich Corp. and the water was deionized water. Twenty weight percent solutions of γ-butyrolactone were used. γ-Butyrolactone contains small amounts of butyric acid and the initial acidity was determined by titrating a sample of the solution with 0.1N aqueous NaOH using phenolphthalein as indicator. Liquid samples removed from the reactor were similarly titrated to determine their acidity. A sample of the initial solution and samples removed from the reactor were also analyzed by Gas Chromatography, (G.C.).

The hydrogenation procedure consisted of adding to the autoclave 0.4 grams of catalyst and 125 g of 20% γ-butyrolactone solution. The autoclave was then closed and pressure tested for leaks with nitrogen. After venting the nitrogen to atmospheric pressure the stirrer was turned on while heating to 240° C. The stirrer was then turned off and with the pressure regulator in the hydrogen line set to 2,000 psig ($1.38 \times 10^7$ Pa), hydrogen was admitted to the reactor and the pressure brought to 2,000 psig ($1.38 \times 10^7$ Pa). The temperature was then adjusted to 250° C. and maintained at 250° C. and 2,000 psig ($1.38 \times 10^7$ Pa). After 45 minutes, the heater, hydrogen feed and stirrer were turned off and samples were taken from the reactor at operating temperature and pressure. The reactor was then cooled to room temperature and then vented to atmospheric pressure and additional samples were taken. Data for catalysts evaluated as described above are presented in Table 1.

TABLE 1

| Ex. No. | Catalyst(a) % on Carbon | | | STY(mol/hr-Kg)(b) THF + BDO | molar selectivity to THF & BDO |
|---|---|---|---|---|---|
| | Ru(c) | Re(d) | Sn(e) | | |
| 1 | 1.0 | 0.77 | 0.00 | 37.4 | 0.70 |
| 2 | 1.0 | 0.77 | 0.43 | 34.4 | 0.89 |
| 3 | 1.0 | 1.50 | 0.00 | 36.7 | 0.87 |
| 4 | 1.0 | 1.5 | 0.29 | 29.1 | 0.92 |
| 5 | 1.0 | 3.08 | 0.00 | 55.6 | 0.88 |
| 6 | 1.0 | 3.08 | 0.57 | 40.8 | 0.94 |
| 7 | 1.0 | 6.0 | 0.9 | 55.5 | 0.95 |
| 8 | 1.5 | 6.0 | 0.9 | 74.5 | 0.95 |
| 9 | 2.0 | 6.0 | 0.9 | 94.9 | 0.93 |

(a) In examples 1–6 the support was particulate Darco KBB carbon, supplied by Norit Americas Inc. The BET surface area was 1,500 $m^2$/g. In examples 7–9 the support was Norit SX2 supplied by Norit Americas Inc, the BET surface area was 900 $m^2$/g.
(b) STY=space-time-yield, (moles of product per Kg of catalyst per hour)
(c) In examples 1 and 2 the ruthenium was reduced in-situ in the reactor, in examples 3–9 the catalyst was reduced in a hydrogen-helium atmosphere ex-situ to the reactor.
(d) In all of the examples $HReO_4$ was used as the rhenium source.
(e) In examples 1 through 6 tin oxalate solution ($SnC_2O_4$) was used as the tin source, in examples 7–9 $SnCl_4$ was used as the tin source.

EXAMPLE 10

This example illustrates the hydrogenation of maleic acid in a continuous bubble column reactor using as catalyst 1.5% Ru, 3% Re, 0.6% Sn/Norit SG carbon supplied by Norit Americas Inc. The catalyst was prepared according to the following procedure: aqueous solutions of $RuCl_3 \cdot xH_2O$ (15.6485 g of 1.0% ruthenium solution), $HReO_4$ (4.1080 g of 8.04% rhenium solution), $SnCl_4 \cdot 5H_2O$ (0.6390 g of 12.5% tin solution) were mixed together and then slowly added while stirring to a beaker containing 10 grams of Norit SG carbon. The mixture was stirred occasionally over about three hours and then dried overnight at reduced pressure (in vacuo) at 110° C. with a nitrogen purge. The oven was cooled to less than 50° C. before removing the catalyst. Reduction of this catalyst was carried out in water at 2,000 lbs ($1.38 \times 10^7$ Pa) pressure in a 125 cc Autoclave Engineers autoclave constructed of Hastelloy C. material. The reduction procedure was carried out as follows: at room temperature 49.88 grams of deionized water was added to the autoclave along with 10 grams of the catalyst described in this example. The autoclave was pressure tested with nitrogen and then the pressure was released and the autoclave was filled with hydrogen gas up to 1,200 pounds ($8.27 \times 10^6$ Pa) pressure. The reactor was then heated to 250° C. while stirring, whereupon at 250° C. the total pressure inside the vessel was about 2,000 pounds ($1.38 \times 10^7$ Pa). The catalyst was reduced under these conditions for about one hour at 250° C. The reactor was then cooled to room temperature, the pressure vented and the catalyst was unloaded. The slurry containing the catalyst was removed and filtered using vacuum and a glass fritted funnel. The solids were dried overnight at 110° C. at reduced pressure (in vacuo) with a nitrogen purge. The oven was cooled to less than 50° C. before removing the catalyst. This catalyst was then tested in the continuous bubble column reactor.

The continuous bubble column reactor consisted of a vertical Hastelloy-C. pipe, ¾" ID by 41.5" long with multiple ports for loading catalyst and reactants and removing products. The reactor was heated continuously and held at 250° C. and maintained at a pressure of 2,000 psig ($1.38 \times 10^7$ Pa) with a constant hydrogen flow. The feed solution, was 40% aqueous maleic acid solution, and the feed rate was 25 cc/hr.

The reaction products exited the reactor by evaporation and an occasional liquid sample was also taken. Samples of the products were analyzed by titration with 0.1N aqueous NaOH to measure acidity and by GC. analysis as previously described for samples from hydrogenations conducted in a batch autoclave. The activity expressed as normalized production rates (STYs) of tetrahydrofuran and γ-butyrolactone over about 200 hours is shown in the Table 2. The combined yield of tetrahydrofuran and useful intermediates, γ-butyrolactone and 1,4 butanediol is also shown in Table 2.

TABLE 2

| Time on Stream (hours) | THF STY | GBL STY | Yield |
|---|---|---|---|
| 96 | 668 | 345 | 0.91 |
| 144 | 709 | 310 | 0.91 |
| 192 | 793 | 310 | 0.92 |

COMPARATIVE EXAMPLE

This example describes a ruthenium, rhenium, supported on carbon catalyst that was run in the continuous bubble column reactor in a similar way to Example 10 for the hydrogenation of maleic acid. The catalyst (1.0% Ru, 6% Re/Darco KBB carbon) was prepared as has been previously described in U.S. Pat No. 5,478 952. This catalyst was then tested in the continuous bubble column reactor. The results of the observed performance in the bubble column reactor are presented below in Table 3.

TABLE 3

| Time on Stream (hours) | THF STY | GBL STY | Yield |
|---|---|---|---|
| 96 | 540 | 202 | 0.79 |
| 144 | 621 | 271 | 0.86 |
| 196 | 529 | 295 | 0.84 |

EXAMPLE 11

This example describes the use of a ruthenium, rhenium and tin supported on carbon catalyst in a novel two-stage process for the production of BDO, THF and GBL in a staged fixed bed system. The reactions were run isothermally. The first reactor was run at 120° C. with 2 grams of a 1.0% Pd/Calgon PCB carbon, and the second reactor was run at 175° C. with 5 grams of 1.0% Ru, 6% Re, 0.9% Sn/Norit ROX carbon. Flowing hydrogen gas and aqueous maleic acid at 30% concentration were fed continuously to the first reactor containing the 1% Pd/carbon catalyst. The hydrogenation products of this first reactor were then fed to the second reactor containing the 1% Ru, 6% Re, 0.9% Sn/Norit ROX carbon catalyst. Gas phase and liquid samples were collected separately and then analyzed by gas chromatography and the liquid sample was titrated for acid. The overall pressure of the system was 3,000 psi ($20.7 \times 10^6$ Pa) and the maleic acid feed rate was 5 mL/hr.

Below is a description of the synthesis of catalysts for both reactors. Synthesis of the 1% Pd/Calgon PCB carbon catalyst involved using 50 g of precalcined Calgon PCB carbon. An aqueous solution of $PdCl_2$, (2.5497 g of a 19.81% Pd solution) was added to the 50 grams of Calgon carbon while stirring well. After the $PdCl_2$ solution was added an additional 45 grams of deionized water was added to the carbon. The mixture was stirred over a three hour period and then dried overnight at 110° C. at reduced pressure (in vacuo) with a nitrogen purge. The oven was cooled to 50° C. and the dried catalyst was removed from the oven.

The Ru, Re, Sn catalyst was made according to the following procedure; 30 grams of Norit ROX carbon was first dried at reduced pressure (in vacuo) at 110° C. prior to use, aqueous solutions of $RuCl_3.xH_2O$ (17.5154 g of 1.86% ruthenium solution), $HReO_4$, (25.2562 g of a 7.74% rhenium solution), and $SnCl_4.xH_2O$, (2.3496 g of a 12.5% tin solution) were mixed together in a beaker and then diluted with 13 grams of additional deionized water. This solution was added slowly while stirring to a beaker containing the carbon. This mixture was stirred occasionally over about three hours. This was then dried overnight at reduced pressure, as previously described.

Both the 2 grams of 1% Pd/Calgon carbon and the 5 grams of 1% Ru,6% Re,0.9% Sn/Norit ROX dried catalysts were loaded into the in series fixed bed microreactors, first and second hydrogenation reactors respectively. The catalysts were reduced simultaneously in series with 40 scc/min of flowing hydrogen using the following protocol. The catalysts were heated under flowing hydrogen to 150° C. at 3,000 psi ($2.07 \times 10^7$ Pa) and 40 scc/min hydrogen flow and then held for one hour under these conditions. The temperature was then increased to 300° C. and then held for three hours under these conditions. After this time period the reactors were cooled to respective run temperatures, i.e. 120° C. for 1% Pd/Calgon catalyst in the first reactor, and 175° C. for the 1% Ru,6% Re,0.9% Sn/Norit ROX carbon catalyst. In Table 4 below are the performance data under the conditions described above.

TABLE 4

| g MAC fed/g Catatyst cumulative | BDO mol % | THF mol % | GBL mol % | Yield |
|---|---|---|---|---|
| 101 | 67.8 | 19.8 | 6.2 | 95 |
| 194 | 61.9 | 21.9 | 8.3 | 94 |
| 301 | 59.3 | 22.5 | 9.2 | 93 |
| 401 | 54.0 | 19.8 | 14.6 | 90 |
| 500 | 53.5 | 22.1 | 13.0 | 90 |

EXAMPLE 12

This example describes the use of a ruthenium and rhenium on carbon supported catalyst in a two-stage process for the production of BDO, THF and GBL as described in more detail in Example 11. The preparation of a 1% Ru,6% Re/Calgon PCB carbon supported catalyst used in the second hydrogenation step is described herein. Aqueous solutions of $RuCl_3.xH_2O$ (12.2254 g of 0.88% ruthenium solution), and $HReO_4$, (8.0200 g of a 8.04% rhenium solution) were mixed together and then added slowly while stirring to a beaker containing 10 grams of precalcined Calgon PCB carbon. The mixture was stirred occasionally over a three hour period and then dried overnight a 110° C. at reduced pressure (in vacuo) with a nitrogen purge. The oven was cooled to 50° C. and the dried catalyst was removed from the oven. Reduction of the catalyst was accomplished in-situ in the reactor similar to what was described above in Example 11. The performance data may be found in Table 5 below:

TABLE 5

| g MAC fed/g Catalyst cumulative | BDO mol % | THF mol % | GBL mol % | Yield |
|---|---|---|---|---|
| 50.1 | 80.7 | 4.38 | 1.01 | 86 |
| 100 | 79.6 | 5.10 | 0.99 | 86 |
| 150 | 81.1 | 4.48 | 3.24 | 89 |

The advantages and benefits of the present invention are felt to be significant and numerous. First and foremost, the trimetallic Ru,Re,Sn/C. catalyst system of the instant invention affords and provides a method for sustaining catalytic hydrogenation of maleic acid or other hydrogenatable precursors dissolved in water with a level of control of selectivity of products amongst the more useful products heretofore unachievable. More specifically in the case of hydrogenating maleic acid and related compounds, the control of production amongst the useful product such as 1,4-butanediol, γ-butyrolactone and tetrahydrofuran is concurrent with reduced relative production of less valuable by-products, such as n-butanol, n-propanol and volatile hydrocarbons such as methane, ethane, propane and butane. The two-stage hydrogenation process of the present invention is particularly useful in controlling the relative distribution (molar ratio) between 1,4-butanediol and tetrahydrofuliran. Thus the selection of the catalyst and the reaction conditions will influence the ultimate molar ratio achieved. The two-stage process further provides an improved method of using the bimetallic Ru,Re/C catalyst system at lower temperatures to achieve high conversion and selectivity. The two-stage process also advantageously allows for the use of more economically available hydrogenation catalyst in the fast hydrogenation of the double bond and independent management of the associated heat of reaction of this step. This process is also amenable to recycle of the intermediate product γ-butyrolactone or alternatively the recovery of γ-butyrolactone thus again affording a level of control of product distribution.

Having thus described and exemplified the invention with a certain degree of particularity, it should be appreciated that the following claims are not to be so limited but are to be afforded a scope commensurate with the wording of each element of the claim and equivalents thereof.

We claim:

1. A method for catalytic hydrogenation of maleic acid in an aqueous solution comprising the steps of:
   (a) hydrogenating maleic acid in an aqueous solution in the presence of hydrogen and a first catalyst to produce an aqueous succinic acid solution;
   (b) hydrogenating said succinic acid solution produced in step (a) in the presence of hydrogen and a second catalyst, said second catalyst consisting essentially of (i) from 0.5 to 10% by weight ruthenium, (ii) from 2.0 to 20% by weight rhenium supported on carbon, said percentages based on total weight of supported catalyst, wherein both ruthenium and rhenium are present in a highly dispersed reduced state and (iii) from 0.1 to 5.0% by weight tin supported on said carbon wherein said carbon support is characterized by a BET surface area of less than 2,000 m²/g, such as to produce a mixture of 1,4-butanediol, γ-butyrolactone, and tetrahydrofluran wherein the selection of said second catalyst and said temperature for the hydrogenation of the succinic acid solution establishes the ratio of 1,4-butanediol to tetrahydrofuran being produced; and then
   (b) recovering at least one product selected from the group consisting of 1,4-butanediol, γ-butyrolactone and tetrahydrofuran.

2. A method of claim 1 wherein said selected temperature for said hydrogenation of succinic acid solution is from 150 to 210° C.

3. A method of claim 1 wherein said selected temperature for said hydrogenation of succinic acid solution is less than 175° C.

4. A method of claim 2 wherein said molar ratio of 1,4-butanediol to tetrahydrofuran produced is from 5:1 to 1:1 across said respective temperature range.

5. A method of claim 1 further comprising the step of removing heat energy from said succinic acid solution during hydrogenation.

6. A method of claim 1 further comprising the step of utilizing heat energy generated in the hydrogenation of maleic acid to succinic acid of step (a) to effect temperature control of the subsequent hydrogenation of succinic acid in step (b).

7. A hydrogenation catalyst consisting essentially of from 0.5 to 10.0% by weight ruthenium, from 2.0 to 20.0% by weight rhenium supported on carbon, said percentages based on total weight of supported catalyst, wherein both ruthenium and rhenium are present in a highly dispersed reduced state and from 0.1 to 5.0% by weight tin supported on said carbon wherein said carbon support is characterized by a BET surface area of less than 2,000 m²/g.

8. A method for catalytic hydrogenation of a hydrogenatable precursor in an aqueous solution comprising the steps of:
   (a) hydrogenating a hydrogenatable precursor in an aqueous solution in the presence of hydrogen and a catalyst, said catalyst consisting essentially of from 0.5 to 10.0% by weight ruthenium, from 2.0 to 20.0% by weight rhenium supported on carbon, said percentages based on total weight of supported catalyst, wherein both ruthenium and rhenium are present in a highly dispersed reduced state and from 0.1 to 5.0% by weight tin supported on said carbon wherein said carbon support is characterized by a BET surface area of less than 2,000 m²/g; and then
   (b) recovering at least one hydrogenated product.

9. A method according to claim 8 wherein the hydrogenatable precursor is selected from the group consisting of maleic acid, maleic anhydride, flumaric acid, succinic acid, the esters corresponding to these acids, γ-butyrolactone and mixtures thereof.

10. A method according to claim 9 wherein said hydrogenating of said hydrogenatable precursor is performed at a temperature above 210° C. and said hydrogenated product is recovered in the vapor phase such as to maximize the amount of tetrahydrofuran.

11. A method according to claim 9 wherein said hydrogenating of said hydrogenatable precursor is performed at a temperature below 210° C. and said hydrogenated product is recovered in the liquid phase such as to maximize the amount of 1,4-butanediol.

* * * * *